United States Patent
Bock et al.

(10) Patent No.: US 8,529,485 B2
(45) Date of Patent: Sep. 10, 2013

(54) MEDICAL APPARATUS FOR EXTRACORPOREAL BLOOD TREATMENT

(75) Inventors: Gerhard Bock, Friedewald (DE); Stefan Moll, Melsungen (DE); Carsten Hasberg, Karlsruhe (DE)

(73) Assignee: B. Braun Medizintechnologie GmbH, Melsungen (DE)

( * ) Notice: Subject to any disclaimer, the term of this patent is extended or adjusted under 35 U.S.C. 154(b) by 879 days.

(21) Appl. No.: 12/377,322

(22) PCT Filed: Jul. 31, 2007

(86) PCT No.: PCT/EP2007/057914
§ 371 (c)(1),
(2), (4) Date: Dec. 23, 2009

(87) PCT Pub. No.: WO2008/022880
PCT Pub. Date: Feb. 28, 2008

(65) Prior Publication Data
US 2010/0087770 A1    Apr. 8, 2010

(30) Foreign Application Priority Data
Aug. 23, 2006  (EP) .................................. 06119406

(51) Int. Cl.
*A61M 37/00*  (2006.01)
(52) U.S. Cl.
USPC .......................................... 604/4.01; 604/6.1
(58) Field of Classification Search
USPC ................................. 604/4.01, 6.05; 382/128
See application file for complete search history.

(56) References Cited

U.S. PATENT DOCUMENTS

| | | | | |
|---|---|---|---|---|
| 6,125,201 | A  * | 9/2000 | Zador | 382/166 |
| 6,594,518 | B1 * | 7/2003 | Benaron et al. | 600/477 |
| 2003/0128125 | A1 * | 7/2003 | Burbank et al. | 340/605 |
| 2003/0194894 | A1 | 10/2003 | Wariar | |
| 2004/0064057 | A1 * | 4/2004 | Siegel | 600/500 |
| 2004/0136580 | A1 * | 7/2004 | Matsumiya et al. | 382/128 |

FOREIGN PATENT DOCUMENTS

| | | |
|---|---|---|
| DE | 40 14 572 A1 | 11/1991 |
| DE | 198 48 235 C1 | 3/2000 |
| EP | 1 574 178 A2 | 9/2005 |
| WO | WO 99/24145 A1 | 5/1999 |
| WO | WO 01/47581 A1 | 7/2001 |
| WO | WO 02/080764 A1 | 10/2002 |
| WO | WO 03/086506 A1 | 10/2003 |
| WO | WO 2004/074822 A1 | 9/2004 |

OTHER PUBLICATIONS

International Search Report, Dated Oct. 18, 2007.

* cited by examiner

*Primary Examiner* — Leslie Deak
*Assistant Examiner* — Sara Sass
(74) *Attorney, Agent, or Firm* — RatnerPrestia

(57) ABSTRACT

The medical apparatus has lines that are connected to the vascular system of a patient. To ensure that an accidental escape of blood is identified, a camera is provided and is directed at the extracorporeal blood circuit of the patient. The image signals from the camera are processed in the sense that the color of blood and/or its arrangement in the image area in the camera image is determined, wherein the size of the recorded image area with the color of blood is also evaluated. In this way, an extracorporeal blood loss can be detected and signaled automatically.

14 Claims, 4 Drawing Sheets

MEDICAL APPARATUS FOR EXTRACORPOREAL BLOOD TREATMENT

FIELD OF INVENTION

The present invention relates to a medical apparatus for extracorporeal blood treatment, comprising a blood treatment device connectable to the blood circuit of a patient via extracorporeal lines, a blood pump, a control unit for controlling said blood pump and for monitoring operational states, and a camera for observation of the extracorporeal blood circuit of a patient present at a treatment station. Particularly, the invention is applicable to a medical apparatus which may happen to cause blood loss to the patient due to leakage in the extracorporeal circuit or due to malfunction at the entrance site to the patient.

A typical case of a blood treatment is the dialysis treatment. Dialysis treatment is normally performed in special buildings. These buildings are normally equipped with 20 to 50 treatment units distributed among several rooms. Since care has to be taken of a plurality of patients, the health care personnel, although in charge of monitoring the patients, does not always have the possibility to be directly present near a given patient. Therefore, use is made of medical appliances which are operative to detect risks to the patient, to perform a corresponding safety control process and to call health care personnel to the patient. For cases of extracorporeal blood loss due to disconnection in the venous return flow, patient safety can presently be guaranteed only through careful observation by the health care personnel because the usual monitoring of the venous pressure is ill-suited to detect a possible blood pressure in each case.

In an extracorporeal blood treatment process, e.g. in hemodialysis or plasma treatment, the blood of a patient is made to flow from an arterial-vessel access site via a filter to venous-vessel access site. An access site to the vascular system is frequently established, through a surgical intervention, in the form of an arterial-venous fistula which normally will be punctured using an arterial or venous cannula. Another option resides in the use of a vessel implant (shunt). A vessel access site as defined herein can be any type of access to the vascular system of a patient and, particularly, the connection between the artery and the vein of the patient. As of yet, an effective safety device for prevention of blood loss during treatment via two cannulae does not exist. Presently, one resorts to the use of adhesive plasters for sealing the lines leading to or from the vessel access site. In conventional dialysis apparatus, when the blood is returned to the patient, the resistance between apparatus and patient is measured. During this process, the blood is supplied via the cannula into the patient at a speed of 200 to 600 ml/min. Already the resistance of the cannula alone is largely within the pressure monitoring range of the dialysis apparatus. If the venous cannula should slide out, blood is caused to flow out from the patient through the arterial access site via the dialysis apparatus. The dialysis apparatus will react on secondary influences such as e.g. on the pressure drop at the venous pressure pick-up. The pressure drop, however, is dependent on the blood flow, the hematocrit, the cannula and the vessel pressure of the patient. In the normal case, the health care personnel will set a lower limiting value to a point as close as possible to the current venous pressure, without having exact knowledge of the pressure occurring if the catheter should slide out of place. In principle, two possibilities exist, notably that the dialysis apparatus emits an alarm without the cannula having slid out, and thus calls the health care personnel to the apparatus, or the dialysis apparatus emits no alarm and the patients suffers a loss of blood.

EP 1 574 178 A1 describes a medical treatment system wherein a video camera is directed towards the treatment station. The image of the video camera is represented on the monitor of a remote doctor's station. In this manner, the physician can visually observe or monitor the patient.

WO 99/24145 A1 describes a pair of electrodes arranged near the cannula and connected to the dialysis apparatus via two lines. In case that the needle should slide out of place, the blood flowing out will cause a conductive connection between the electrodes. This condition is detected by the dialysis apparatus. The control unit of the dialysis apparatus will stop the blood flow and alarm the personnel. This method requires additional manipulations which have to be carried out by the personnel with great diligence. Further, false alarms may be caused by sweat accumulating between the electrodes.

WO 01/47581 A1 describes an electrode arrangement. This arrangement can improve the detection by causing the current to be capacitively coupled in between the arterial and the venous line with the aid of a generator. What is evaluated is the voltage drop generated by the blood flow in the line. Should any one of the cannulae slide out, the current is reduced, which will be detected. A disadvantage of this method resides in that a needle which has not fully slid out cannot be detected.

DE 198 48 235 C1 represents a system which is operative to evaluate the arterial and the venous pressure so as to detect the sliding-out of the cannula on this basis. This method suffers from the disadvantage that also the dynamic behavior of the extracorporeal circuit will be included in the evaluation, thus involving the risk of faulty evaluations. Neither does this method solve the problem of an indirect measurement of the blood loss because the extracorporeal pressure is not a measure for blood loss.

WO 03/86506 A1 describes an electric contact to be directly inserted into the blood. By use of a constant current and through evaluation of the voltage drop, it is detected whether the cannula has slid out. Also here, the disadvantage exists that a cannula which has not yet fully slid out cannot be detected.

SUMMARY OF INVENTION

It is an object of the invention to design a medical apparatus with extracorporeal blood circuit in such a manner that an excessive blood loss suffered by the patient during treatment will be detected with high reliability.

The medical apparatus according to the present invention is characterized by claim 1. Said apparatus comprises a camera for color images which is connected to a detection device for detecting the color of blood and the size of the image area occupied by the blood. The camera is directed onto the treatment place and respectively onto the patient placed thereon. The camera is operative to take pictures whose color information is evaluated by an analyzing device. In the evaluation process, leaking or leaked blood will be detected by its typical color. The quantity of the leaked blood is detected on the basis of the image area occupied by the blood.

The surface occupied by the blood does not necessarily have to be cohesive but can also be composed of a plurality of individual surfaces.

The evaluation device receiving the camera images is provided to perform the following processes:

taking digital pictures of the patient and the extracorporeal circuit, transfer of pixel information into a color space which allows for a distinction between skin and blood, classification of pixels as blood or non-blood, summation of blood pixels, comparing the summed pixels to a limiting value, alternatively, detecting blood stains and evaluating their enlargement, stopping the blood pump and closing the tube clamp if the limiting value has been exceeded, and emitting an alarm.

The blood access devices are normally applied to the lower arm of the patient. From there, tubes extend to the medical apparatus (e.g. dialyzer). The blood access devices are adhered to the patient's arm with the aid of plasters. A leakage of blood occurring at one of the blood access devices is located in the immediate vicinity of the patient's body; thus, in the camera image, it is imperative to differentiate between the blood and the skin of the patient.

Depending on the respective quantity of the blood lost, the blood loss may in fact be lethal. In risk assessment, a lethal effect is assumed to occur at a value of about 500 ml. In the given case, the lethal value will depend on the individual physical condition of the patient.

As a precondition for a safe detection of faulty blood access sites, the blood access sites have to be visible to the camera. This means that the patient should not cover the blood access sites with a blanket or the like.

When use is made of a digital camera, the surface covered by leaking blood is detected on the basis of those exposed pixels which receive the color of the blood. The number of blood pixels can be set into relation to the total number of the pixels of the camera image.

The images generated by a digital camera are normally present in the RGB format (color space). Each picture element (pixel) is composed of three values by which the colors red, green and blue are weighted or represented in their intensity. Each weighting is in a range between 0 and 255. Per component of the color feature vector, there will result 8 bits, which is to say 3×8 bits=24 bits per pixel. An easily intelligible representation of this color space is the RGB color cube. Involved herein is the possibility of about 16 million colors. On the main diagonal, the grey values from black (0, 0, 0) to while (255, 255, 255) are found. Examples of further colors are red at (255, 0, 0) and yellow (255, 255, 0).

For blood detection, the RGB format is not particularly well suited because it is difficult to define concrete boundaries. Thus, according to a preferred embodiment of the invention, a transformation device is provided by which the signals emitted in the RGB color space are transformed into another color space. Said other color space will preferably be the YUV color space. This transformation makes it possible to achieve a better distinction between blood and non-blood pixels.

The YUV color space consists of a brightness component Y and two color components U and V. The YUV color space is obtained from the RGB color space by linear transformation:

$$\begin{pmatrix} Y \\ U \\ V \end{pmatrix} = \begin{pmatrix} 0.299 & 0.587 & 0.114 \\ -0.148 & -0.289 & 0.437 \\ 0.615 & 0.515 & -0.100 \end{pmatrix} \cdot \begin{pmatrix} R \\ G \\ B \end{pmatrix}$$

By the rotational matrix, the main diagonal of the RGB color space (grey values) is mapped onto the Y axis of the YUV color space. The objective resides in effecting a separation between color and brightness information. The ranges of values extend from 0 to 255 for the Y-component and from −128 to +127 for the U- and V-components.

The color information is stored in the U- and V-components, and the brightness information, largely depending on the prevailing illumination, is stored in the Y-component.

Examples of the definition of the limiting values or criteria in the YUV color space will be described farther below.

The criteria for the blood discrimination depend on the illumination spectrum of the respective illumination at the time that the image is captured by the camera. Thus, for instance, neon light requires different limiting values or limiting criteria than light generated by light bulbs, or daylight. The detection of the respective type of illumination may require the use of an illumination sensor which will control a device for selecting the stored criteria in dependence on the detected illumination spectrum.

By way of alternative, it is possible to perform the illumination with a defined illumination spectrum and to use a specially defined illumination source for capturing the camera images. This illumination source can consist e.g. of a flashlight device having an illumination strength sufficient to supersede extraneous light, so that the evaluation of the color spectrum of a pixel image can be carried out on the basis of the illumination spectrum of the defined illumination source.

The invention also makes it possible, using the camera, to detect the propagation speed of a blood stain by detecting and respectively computing the increase of the blood-colored surface area within a defined time period. In this type of evaluation, it can also be provided that the image sequence of the camera is automatically accelerated in case of a high propagation speed of the blood.

The loss of blood can also be detected by providing a device performing a summation of the image pixels or of a blood-colored surface area over a plurality of images of the camera, for thus detecting the blood loss. Also the contour of the surface (or of plural surfaces) occupied by blood can be included into this detection process.

For safeguarding that the camera-based monitoring for possible leakage of blood will be performed only when the patient has been connected to the extracorporeal tube system and blood is flowing into the patient, the extracorporeal line system can be provided with a blood detector allowing the camera to be activated only in case of detection of blood. This blood detector can be e.g. a red-color detector for detection of red liquid in the tube system.

To allow the camera to capture the correct target area, the camera can be provided with a drive unit for self-adjustment which will adjust the camera to a reference marking. This reference marking, formed e.g. as a tag or a button, is to be attached on the target area such as the patient's lower arm, for instance. Should no reference marking be detected, an alarm will be triggered.

Transmission of the images from the camera to the apparatus is performed via cable or through a wireless connection. It is also possible to provide a plurality of cameras for capturing the target area from different perspectives.

The apparatus preferably includes a reading device for reading an identification code of the operating personnel, said identification code being provided e.g. on machine-readable staff ID card. The data of this identification will be stored so as to keep a documentation indicating the respective person who operated the apparatus, the time this was performed and the settings which were made.

The reading of said identification code also provides an indication that a member of the health care personnel is present at the treatment station. This indication can be useful for the evaluation of the signals indicative of blood loss. Thus, for instance, it is possible to consider only the hitherto existing blood surface area as a reference value, with the effect that only those changes will be registered which occurred since the appearance of the health care person.

Using the method of the invention, also extracorporeal blood circuits of a type wherein no blood treatment is performed can be monitored for leaks. Examples of such cases are the taking of blood and a blood circuit system during a surgical intervention.

Embodiments of the invention will be explained in greater detail hereunder with reference to the drawings.

DETAIL DESCRIPTION

Figure 1:
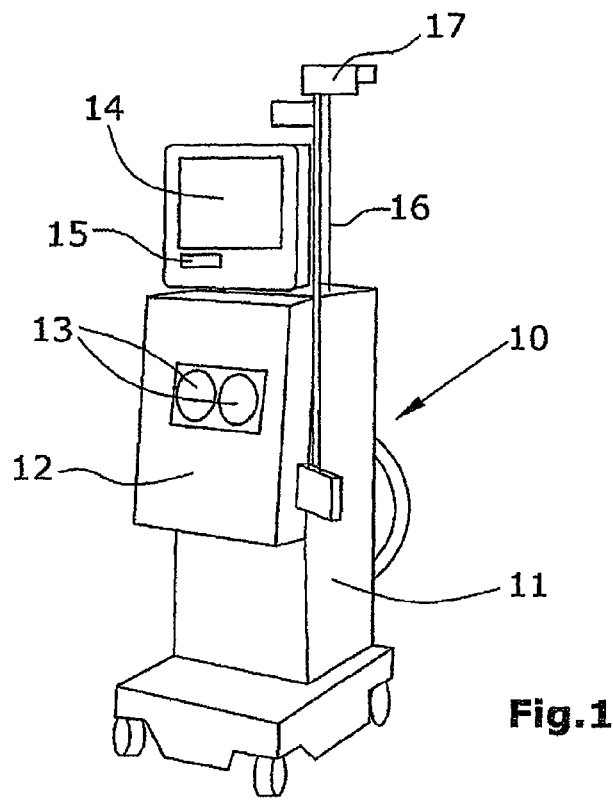
FIG. 1 is a perspective view of said medical apparatus in the form of an apparatus for hemodialysis, hemofiltration or plasma treatment.

FIG. 1 illustrates a medical apparatus 10 for extracorporeal blood treatment. Said apparatus comprises an apparatus cabinet 11 accommodating the mechanical components and supporting, on its front, a console 12 with two blood pumps 13 arranged therein which are accessible from outside. The blood pumps are hose pumps, their hoses being inserted from the front.

Arranged on the top of said apparatus cabinet 11 is a control unit 14 which also forms the interface for communication with the user. For this purpose, control unit 14 comprises a touchscreen monitor allowing the user to call up various menus, to check operational conditions and to input data and orders. Further provided is a card reader 15 into which the user can insert a machine-readable identification card.

A camera 17 is fastened to an infusion support bar 16. Said camera is a digital camera for color images. The images recorded by camera 17 are transmitted to control unit 14. Camera 17 is directed towards a patient treatment station, e.g. onto a couch on which the patient is lying while undergoing blood treatment. In this manner, the extracorporeal circuit is captured by the camera image.

The patient's body is connected to apparatus 10 via tubes. An arm of the patient is connected to an arterial access device 20 and a venous access device 21. An arterial tube conduit 22 extends from said arterial access device 20 to a blood pump 13. Said blood pump is provided for pumping the blood through the blood chamber 25a of a treatment apparatus consisting of a dialyzer, the two chambers 25a,25b of the latter being separated by a membrane 26. Chamber 25b is a dialyzing liquid chamber having the dialyzing liquid flowing therethrough.

After leaving said chamber 25a, the blood will flow into a venous tube conduit 23 connected to venous access device 21. In this manner, a blood circuit is formed.

Said arterial line 22 is provided with a pressure sensor 27 for measuring the arterial blood pressure. In a similar manner, said venous line is provided with a pressure sensor 28 for measuring the venous blood pressure. Venous line 23 further includes a red-light detector 29 for detecting the presence of blood in the tube conduit and for communicating this state to control unit 14. Also said pressure sensors 27,28 are connected to control unit 14. The latter is used for controlling the whole operation of the apparatus and for monitoring the above described functions as well as various other function which will not be explained in greater detail here.

To be able to shut off the blood circuit, the venous line 23 is provided with a tube camp 30 controlled by control unit 14. Also the arterial line 22 is provided with a shut-off means consisting of said blood pump 13. This blood pump is a hose pump which is continuously squeezed by a squeezing member. When the blood pump is at a standstill, the pump acts as a shut-off means for closing the hose conduit.

Figure 2:
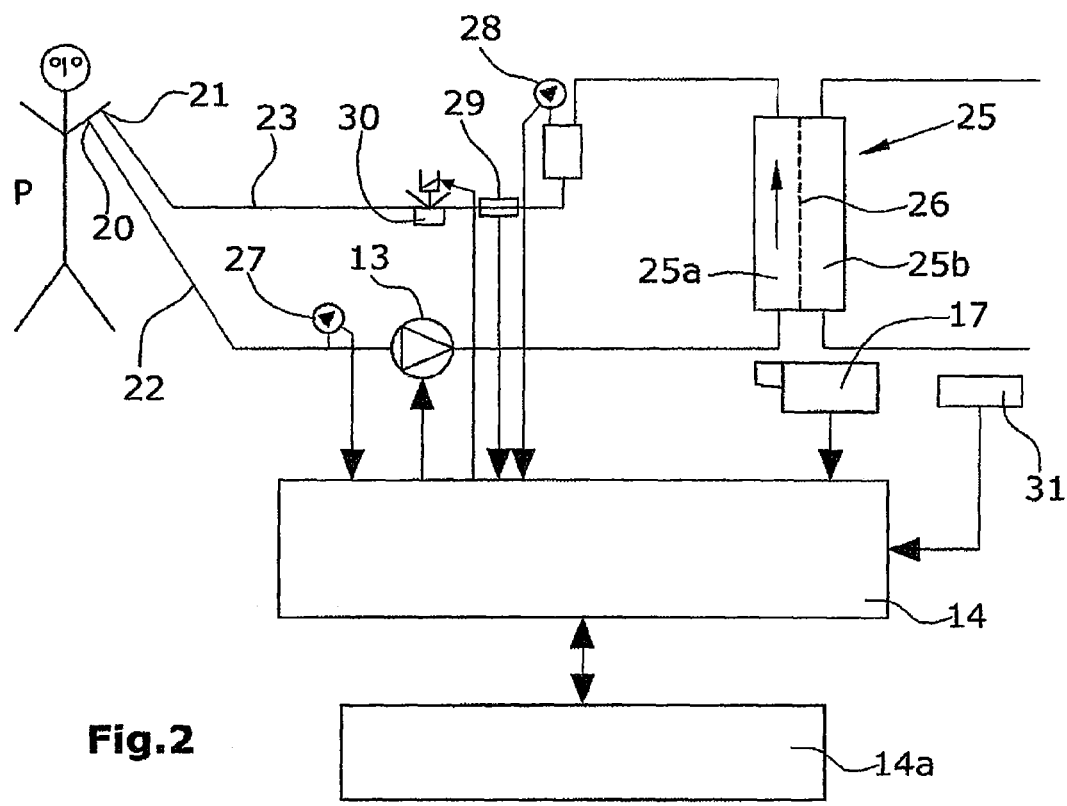
FIG. 2 is a schematic representation of the essential functional components of a dialysis apparatus.

Camera 17 and its connection to control unit 14 are schematically indicated in FIG. 2. Further provided is an illumination sensor 31 for detecting the type of the illumination light, e.g. neon light, light including a UV light portion or warm lamplight. In dependence thereon, the criteria for blood detection will be changed.

Figure 3:
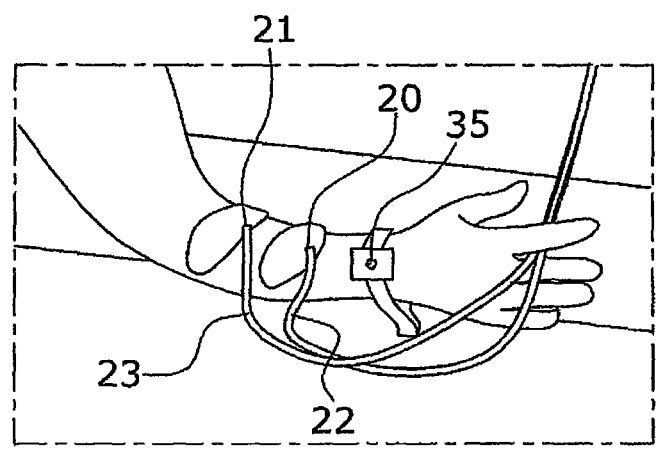
FIG. 3 is a representation of a patient's arm provided with access devices, as captured by the camera.

FIG. 3 shows the image of the to-be-observed area captured by camera 17. Fastened to the arm of the patient, who is lying on a treatment place, are the vessel access devices 20,21, with the hose conduits 22,23 leading from these to the blood pump. On the patient's body, i.e. on the arm in the instant case, a reference marking 35 is attached which can be detected by camera 17. By a motion drive means (not shown), camera 17 is adjusted to the effect that the reference marking 35 will be arranged at a specific spot in the camera image. In this manner, it is safeguarded that the camera is at all times kept directed onto the target area, irrespective of movements of the patient.

Control unit 14 in FIG. 2 is a computer with storage unit. The control unit also performs all monitoring and control processes and further initiates the alarm. Control unit 14 is connected to a display, operating and communication unit 14a.

When a patient is to undergo dialysis, the blood pump is used to build up an extracorporeal blood flow of 50 to 600 ml/min. by sucking the blood from the arterial cannula with the aid of a hose pump and returning the blood via the venous cannula. The blood is conveyed in lines connected to the components such as e.g. the cannulae, the pressure sensor and the dialyzer. The controlling and monitoring processes are performed by means of a control, computer and storage unit. The parameters for the patient under treatment will be input via said display, operating and communication unit. For interrupting the blood flow, the control unit will stop the blood pump and close the hose clamp. Additionally, an optical and acoustic alarm will be triggered. In this manner, the patient is protected from further damage because a further blood loss is precluded.

The images generated by the digital camera are normally provided in RGB format. Each individual pixel is composed of three values by which the colors red, green and blue are weighted. Each weighting is in a range between 0 and 255. Using a transformation device, the image contents present in the RGB color space are transformed into another color space. The latter preferably is a YUV color space which is better suited for blood detection. The purpose of said transformation is to establish a distinction between blood pixels and non-blood pixels. Apart from the YUV color space, also other color spaces such, e.g. HSV and Lab, can be used.

Figure 4:
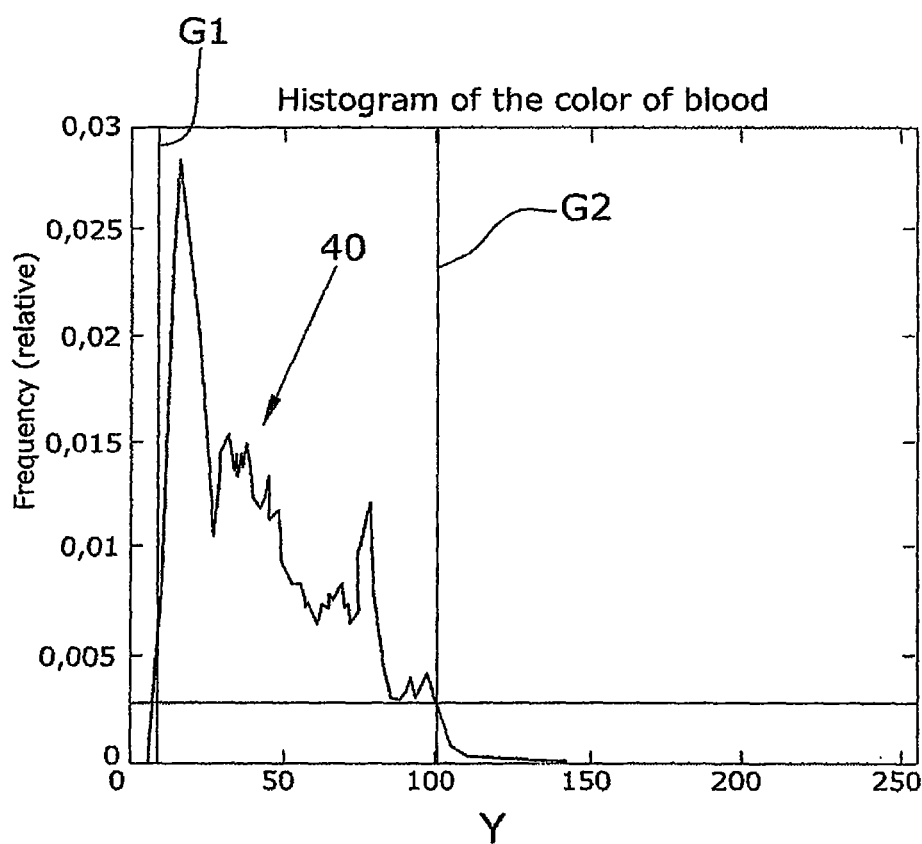
FIGS. 4-6 are histograms of the color of blood in the YUV color space, along with examples of limiting values used as criteria for blood detection, wherein U and V are shifted by +128.
Figure 5:
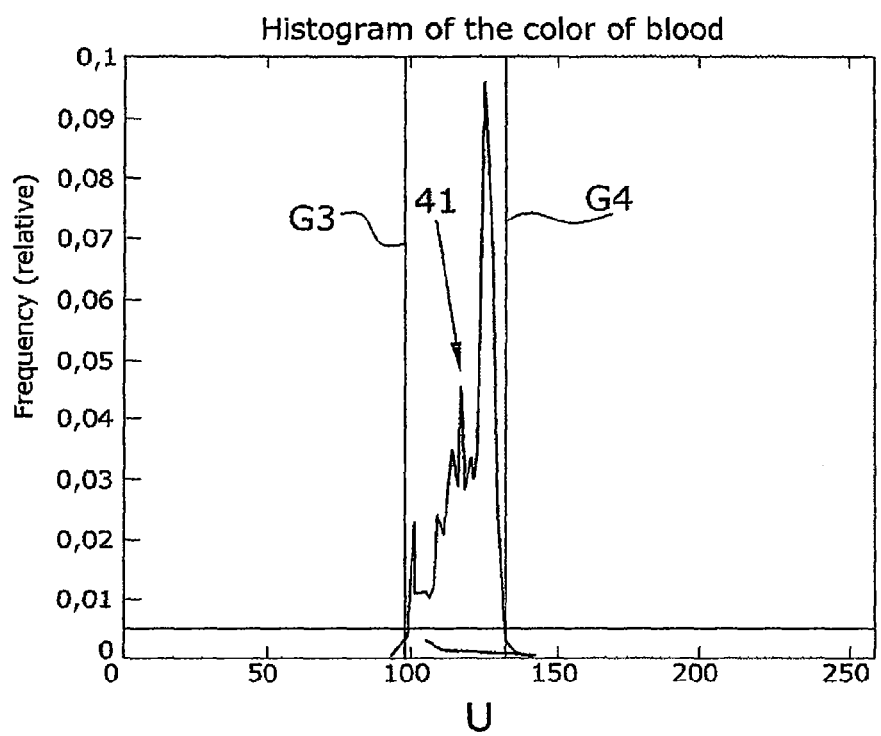
Figure 6:
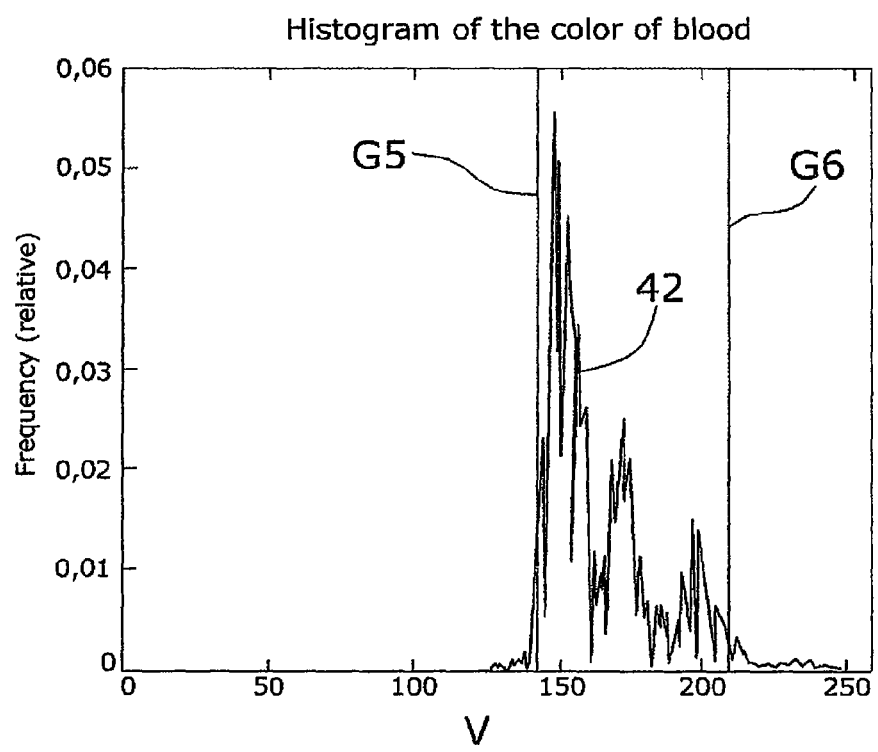

For delimitation between blood-color pixels and non-blood-color pixels, sharply distinctive boundaries are introduced into the color space. If the pixel under examination is arranged within the subspace marked by the boundaries, it will be classified as a blood pixel. The limits or criteria of the components Y, U and V are obtained on the basis of data acquired by learning which are recorded while blood is being observed under various illumination spectra. FIGS. 4, 5 and 6 show various recorded histograms at a specific illumination. In these Figures, the values Y, U and V are respectively plotted along the abscissa, and the relative frequency is plotted along the ordinate. The U- and V-axes are shifted by respectively +128.

The curve 40 in FIG. 4 shows the frequency distribution of the brightness value Y for blood. It is evident that blood may exist in case of values between G1=10 and G2=100.

FIG. 5 shows the frequency distribution 41 for the value U in blood. The curve 41 extends between the limits G3=96 and G4= about 130.

FIG. 6 shows the frequency distribution 42 for V of G5=140 to G6=210.

Figure 7:
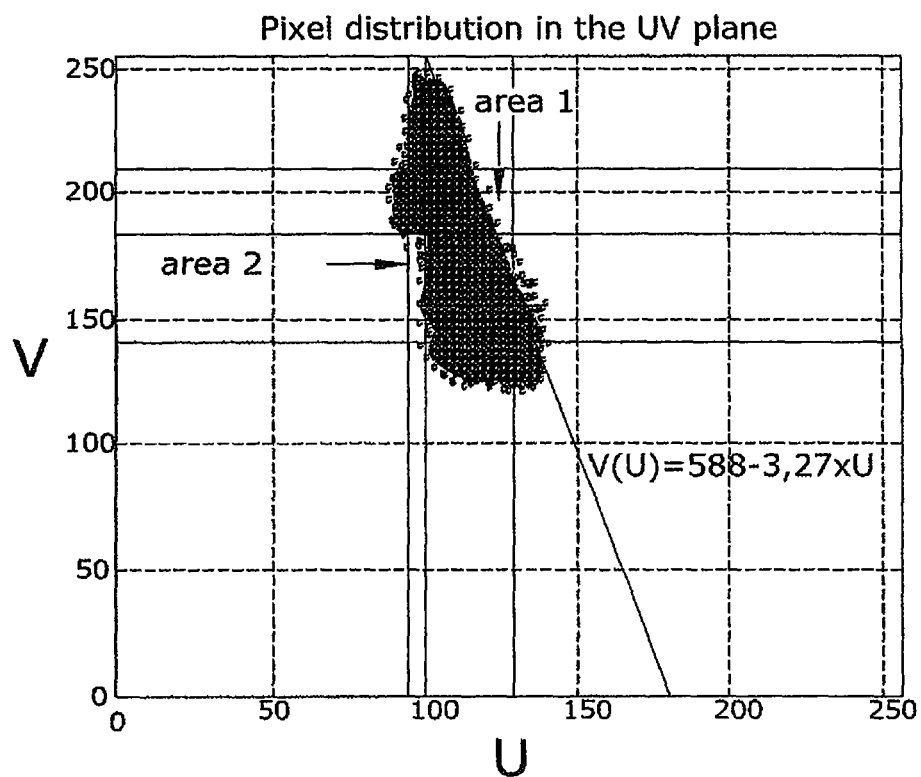
FIG. 7 shows an example of a pixel distribution in the UV plane, along with examples of limiting values.

FIG. 7 shows the pixel distribution of blood in the UV plane.

The most massive disturbing factor in the process of distinguishing whether or not a pixel is indicative of blood is constituted by the skin. For elimination of this disturbing factor, it has turned out that the YUV color space provided with a sharp boundary at the Y-component has is well-suited for differentiating between blood and skin.

Figure 8:
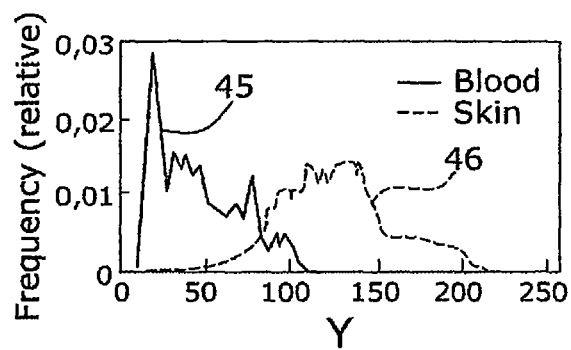
FIG. 8 is a diagram of frequencies across the brightness component Y in the YUV color space for the evaluation of blood and skin.

FIG. 8 shows the frequency distribution of the component Y, with the curve 45 representing blood and the curve 46 representing the color of skin. Except for an overlap region, both curves can be easily distinguished.

For evaluating the pixels, the following types of modeling can be applied:

Explicit YUV
  P1: Y_[10, 90]
  P2: U_[96, (588−V)/3.27]
  P3: U_[102, (588−V)/3.27]
  P4: V_[184, 242]
  P5: V_[140, 184]
  R: If [P1 and [(P2 and P4) or (P3 and P5)]], then [pixel=blood]

In the above formulation, the parameter P1 consists in that Y is between 10 and 90. Rule R indicates those conditions which must be satisfied so that a pixel of the camera image is detected as representative of blood, and involves a Boolean logical link.

Non-parametric UV/explicit Y
  This approach combines the non-parametric modeling of the UV components with an explicit modeling of the Y component. The evaluation of the non-parametric model is performed on the basis of a limiting value. If the value exceeds a predefined limiting value and if Y_[10, 90] is satisfied, the pixel will be classified as a blood pixel.

Parametric UV/explicit Y
  This approach combines the parametric modeling of the UV components with an explicit modeling of the Y component. The evaluation of the parametric model is performed on the basis of the Mahalanobis distance. If the computed distance is below a predefined limiting value and if Y_[10, 90] is satisfied, the pixel will be classified as a blood pixel.

Parametric YUV
  In this approach, all three color space components are modeled with the aid of a Gaussian distribution. For the parameters of the Gaussian distribution, use is made of said learned data. The evaluation is performed on the basis of the Mahalanobis distance. If the distance between pixel and Gaussian distribution is smaller than a limiting value, this pixel will be classified as a blood pixel.

Identical or similar rules can be established also for the other color spaces, while utilizing the principle of learned data (reference). Further, it is possible, for image-taking, to emit from the camera a specific light (between infrared and ultraviolet).

For further evaluation of the obtained blood pixel, two solutions are applicable. Both solutions are based on the principle of image sequence. This means that images are taken at an interval of several seconds and that the evaluation of the current image will be derived from the history. In this method, the blood pixels, in the form of a sum or a surface area, will be used as a measure of the blood loss. To avoid false alarms, reference markings to be scanned by a camera or a laser beam can be applied, with the camera being able to focus on them.

Further, with reference to said classified blood pixels in the image sequence, it has to be determined whether or not an extracorporeal leakage of blood exists.

In this process, the following steps are executed:
1. Taking an image of the blood
2. Classification of the blood pixels in the image
3. Evaluation of the image sequence of the classified blood pixels The third step will result in the decision as to whether or not a critical blood loss has been reached. Using the following relation, the maximum time period between two images is detected:

$$\Delta t = \frac{Q_{blood\_extracorporeal}}{V_{blood\_critical}}$$

From the relationship between the volume of the leaked blood $V_{blood}$ and the blood surface area $A_{blood}$ resulting therefrom, a factor x can be obtained which represents the propagation speed of the blood. Said factor x for the propagation speed, i.e. surface area per volume, is dependent on the nature of the surface on which the blood is spreading, and will be gathered from a table:

$$X = \frac{A_{blood}}{V_{blood}}$$

The pixels in the image which are visual representations of a blood stain, are set into relation on the basis of the relationship between the surface area of the recorded image portion and the resolution of the camera. In a camera with a number of pixels $N_{image}$, the following relation is obtained for the number of blood pixels:

$$N_{blood(t)} = \frac{N_{image}}{A_{image}} \cdot x \cdot Q_{blood\_loss} \cdot t$$

$N_{blood(t)}$ herein denotes the number of pixels of the color of blood, $A_{image}$ denotes the image surface area, and $Q_{blood\_loss}$ denotes the leaked blood flow, with t denoting the time.

Between two images, the blood loss ΔV is obtained from the following calculation:

$$\Delta V_{blood\ loss(k)} = (N_{blood(k)} - N_{blood(k-1)}) \cdot \frac{A_{image}}{N_{image} \cdot x}$$

Herein, k denotes the current number of an image.

In the above context, it is assumed that no blood loss has occurred before connecting the patient to the extracorporeal circuit. The starting of the camera and respectively the evaluation of the images is performed manually and/or by sensors and/or on the basis of operational conditions which are indicative of an extracorporeal blood flow. The blood flow is obtained from the sum of the delta volumes up to the first image, or up to that image wherein the presence of operating personnel is sensed. The sensing of a member of the operating personnel is performed through image detection by the camera, identification by chip card, key input, or the like.

The extracorporeal blood flow will be stopped and an alarm will be triggered if the sum of the blood loss is larger than a predefined limiting value.

Abnormal conditions such as
a) temporary obstruction of the view onto the monitored image portion,
b) movement of the patient and resultant change of the image portion,
c) emergence of blood-like stains (on printed publications, pieces of clothing)

can be processed by logical comparisons during image evaluation as described hereunder, so as to avoid false alarms.

1. Should the number of blood pixels drop drastically, there is issued an indication prompting the personnel to readjust the camera (case a).
2. A negative blood loss (less blood pixels than in the starting image) will be ignored or be set as a starting image (case b).
3. If a larger blood loss (blood pixels) occurs than extracorporeally conveyed, this will be ignored, and an indication will be emitted for prompting the personnel to perform corrective measures (case c).
4. In case b, compensation can be carried out through a motor-steerable camera wherein the camera is adjusted with the aid of an image detection unit or a marking.
5. If individual blood pixels are not situated in a surface arrangement, these will be ignored in the evaluation.

The invention claimed is:

1. A medical apparatus for extracorporeal blood treatment, comprising:
   a treatment device connectable to a blood circuit of a patient via extracorporeal lines, at least one blood pump,
   a camera configured to capture an image of an extracorporeal treatment station, characterized in that said camera is a color camera; and
   a control unit coupled to the at least one blood pump and the camera, wherein the control unit is configured to identify a blood colored surface area within the image, to calculate a size of the blood colored surface area within the image and a speed of the enlargement of the blood colored surface area within the image, and to shut off the blood circuit if a limiting value of the speed of the enlargement of the blood colored surface area has been exceeded.

2. The medical apparatus according to claim 1, characterized in that said camera is a digital camera and that means are provided for detecting the number of pixels exposed by the color of blood.

3. The medical apparatus according to claim 1, characterized in that a transformation device is provided for transforming the signals of said camera emitted in the RGB color space into another color space.

4. The medical apparatus according to claim 3, characterized in that said other color space is the YUV color space.

5. The medical apparatus according to claim 1 characterized by a storage unit for storage of criteria for blood detection.

6. The medical apparatus according to claim 5, characterized in that said storage unit has different criteria stored therein for different illumination spectra.

7. The medical apparatus according to claim 5, characterized by an illumination sensor for detecting the illumination spectrum and by means for selecting said stored criteria in dependence on the detected illumination spectrum.

8. The medical apparatus according to claim 1 characterized in that an illumination device is provided for illuminating the area captured by the camera with light having a predetermined illumination spectrum.

9. The medical apparatus according to claim 1 characterized by a device for computing the speed of the enlargement of the blood-colored surface area.

10. The medical apparatus according to claim 9, characterized in that the image sequence of the camera is controlled in correspondence to the speed of the enlargement of the blood-colored surface area.

11. The medical apparatus according to claim 1, characterized in that, for detecting the blood loss, a device is provided for summation of the blood-colored image pixels over a plurality of images of the camera.

12. The medical apparatus according to claim 1, characterized in that the extracorporeal line system includes a blood detector allowing for activation of the camera upon detection of blood.

13. The medical apparatus according to claim 1, characterized in that the camera is provided with a drive unit for self-adjustment and is operative to adjust itself towards a reference marking.

14. The medical apparatus according to claim 13, characterized in that an alarm is generated in case that the camera does not find said reference marking.

* * * * *

UNITED STATES PATENT AND TRADEMARK OFFICE
CERTIFICATE OF CORRECTION

PATENT NO. : 8,529,485 B2　　　　　　　　　　　　　　　　　　　　　　　　Page 1 of 1
APPLICATION NO. : 12/377322
DATED : September 10, 2013
INVENTOR(S) : Bock et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1185 days.

Signed and Sealed this

Fifteenth Day of September, 2015

Michelle K. Lee
*Director of the United States Patent and Trademark Office*